(12) United States Patent
Baarman

(10) Patent No.: US 7,953,369 B2
(45) Date of Patent: May 31, 2011

(54) SYSTEM AND METHOD FOR INDUCTIVE POWER SUPPLY CONTROL USING REMOTE DEVICE POWER REQUIREMENTS

(75) Inventor: David W. Baarman, Fennville, MI (US)

(73) Assignee: Access Business Group International LLC, Ada, MI (US)

( * ) Notice: Subject to any disclaimer, the term of this patent is extended or adjusted under 35 U.S.C. 154(b) by 129 days.

(21) Appl. No.: 12/370,169

(22) Filed: Feb. 12, 2009

(65) Prior Publication Data

US 2009/0212628 A1    Aug. 27, 2009

Related U.S. Application Data

(63) Continuation of application No. 10/689,148, filed on Oct. 20, 2003, now Pat. No. 7,522,878, which is a continuation-in-part of application No. 10/175,095, filed on Jun. 18, 2002, now Pat. No. 6,673,250, which is a continuation-in-part of application No. 09/592,194, filed on Jun. 12, 2000, now Pat. No. 6,436,299.

(60) Provisional application No. 60/444,794, filed on Feb. 4, 2003, provisional application No. 60/140,159, filed on Jun. 21, 1999, provisional application No. 60/140,090, filed on Jun. 21, 1999.

(51) Int. Cl.
*H04B 5/00* (2006.01)

(52) U.S. Cl. ....... 455/41.1; 455/571; 455/572; 455/573; 455/127.1; 363/16; 363/17; 363/24; 363/26; 363/97; 307/104; 307/145; 307/149; 307/155

(58) Field of Classification Search .......... 455/41.1, 455/571–572, 573, 127.1; 363/21.02, 15–17, 363/24–26, 97; 307/145, 155–156, 149; 235/492; 251/129.04; 710/72–74

See application file for complete search history.

(56) References Cited

U.S. PATENT DOCUMENTS

| | | | |
|---|---|---|---|
| 3,949,268 A | 4/1976 | von Mangoldt | |
| 4,076,996 A | 2/1978 | Maehara | |
| 4,800,328 A | 1/1989 | Bolger et al. | |
| 4,818,855 A | 4/1989 | Mongeon et al. | |
| 5,070,293 A | 12/1991 | Ishii et al. | 320/108 |
| 5,122,729 A | 6/1992 | Itoga et al. | |

(Continued)

FOREIGN PATENT DOCUMENTS

EP    0178852    4/1986

(Continued)

OTHER PUBLICATIONS

Gulko, Michael, et al, Inductor-Controlled Current-Sourcing Resonant Inverter and its Application as a High Pressure Discharge Lamp Driver, IEEE, pp. 434-440, May 1994.

(Continued)

*Primary Examiner* — Marceau Milord
(74) *Attorney, Agent, or Firm* — Warner Norcross & Judd LLP

(57) ABSTRACT

An adaptive inductive ballast is provided with the capability to communicate with a remote device powered by the ballast. To improve the operation of the ballast, the ballast changes its operating characteristics based upon information received from the remote device. Further, the ballast may provide a path for the remote device to communicate with device other than the adaptive inductive ballast.

29 Claims, 9 Drawing Sheets

U.S. PATENT DOCUMENTS

| | | | | |
|---|---|---|---|---|
| 5,229,652 | A | 7/1993 | Hough | |
| 5,325,046 | A | 6/1994 | Young et al. | |
| 5,341,280 | A | 8/1994 | Divan et al. | |
| 5,367,242 | A | 11/1994 | Hulman | |
| 5,428,659 | A | 6/1995 | Renner et al. | |
| 5,455,466 | A | 10/1995 | Parks et al. | 307/104 |
| 5,455,467 | A | 10/1995 | Young et al. | 307/104 |
| 5,476,488 | A | 12/1995 | Morgan et al. | |
| 5,493,287 | A | 2/1996 | Bane | |
| 5,550,452 | A | 8/1996 | Shirai et al. | |
| 5,596,567 | A | 1/1997 | deMuro | |
| 5,600,225 | A | 2/1997 | Goto | |
| 5,734,254 | A * | 3/1998 | Stephens | 320/106 |
| 5,777,861 | A | 7/1998 | Shimizu et al. | |
| 5,796,334 | A * | 8/1998 | Chen et al. | 340/539.3 |
| 5,814,900 | A | 9/1998 | Esser et al. | |
| 5,831,348 | A * | 11/1998 | Nishizawa | 307/104 |
| 5,889,384 | A * | 3/1999 | Hayes et al. | 320/108 |
| 5,905,372 | A | 5/1999 | Kuffner et al. | |
| 5,929,604 | A | 7/1999 | Irvin | 320/136 |
| 5,963,012 | A * | 10/1999 | Garcia et al. | 320/106 |
| 5,982,764 | A | 11/1999 | Palermo et al. | |
| 5,983,076 | A | 11/1999 | Takasan et al. | 455/41.1 |
| 6,057,668 | A | 5/2000 | Chao | 320/108 |
| 6,118,249 | A * | 9/2000 | Brockmann et al. | 320/108 |
| 6,127,799 | A * | 10/2000 | Krishnan | 320/104 |
| 6,151,222 | A | 11/2000 | Barrett | |
| 6,173,899 | B1 | 1/2001 | Rozin | 235/492 |
| 6,184,651 | B1 * | 2/2001 | Fernandez et al. | 320/108 |
| 6,252,380 | B1 * | 6/2001 | Koenck | 320/150 |
| 6,265,791 | B1 | 7/2001 | Eberl et al. | |
| 6,301,128 | B1 * | 10/2001 | Jang et al. | 363/17 |
| 6,323,775 | B1 | 11/2001 | Hansson | |
| 6,374,169 | B1 | 4/2002 | Demay et al. | 701/50 |
| 6,415,388 | B1 | 7/2002 | Browning et al. | 713/322 |
| 6,424,124 | B2 * | 7/2002 | Ichihara et al. | 320/149 |
| 6,429,622 | B1 | 8/2002 | Svensson | |
| 6,436,299 | B1 | 8/2002 | Baarman | |
| 6,462,432 | B1 | 10/2002 | Seelig et al. | |
| 6,548,985 | B1 | 4/2003 | Hayes et al. | |
| 6,597,076 | B2 * | 7/2003 | Scheible et al. | 307/104 |
| 6,636,146 | B1 | 10/2003 | Wehoski | 340/10.4 |
| 6,657,351 | B2 * | 12/2003 | Chen et al. | 310/171 |
| 6,704,608 | B1 | 3/2004 | Azuma | 700/66 |
| 6,751,691 | B1 | 6/2004 | Douglas | 710/73 |
| 6,756,697 | B2 | 6/2004 | Mizutani et al. | 307/10.1 |
| 6,825,620 | B2 * | 11/2004 | Kuennen et al. | 315/224 |
| 6,906,495 | B2 | 6/2005 | Cheng et al. | 320/108 |
| 6,934,167 | B2 | 8/2005 | Jang et al. | 363/21.02 |
| 7,054,965 | B2 | 5/2006 | Bell et al. | 710/72 |
| 7,065,658 | B1 | 6/2006 | Baraban et al. | 713/300 |
| 7,110,269 | B2 | 9/2006 | Cao et al. | |
| 7,132,918 | B2 * | 11/2006 | Baarman et al. | 336/188 |
| 7,180,248 | B2 * | 2/2007 | Kuennen et al. | 315/224 |
| 7,212,414 | B2 * | 5/2007 | Baarman | 363/16 |
| 7,375,492 | B2 * | 5/2008 | Calhoon et al. | 320/108 |
| 7,375,493 | B2 * | 5/2008 | Calhoon et al. | 320/108 |
| 7,378,817 | B2 * | 5/2008 | Calhoon et al. | 320/108 |
| 7,382,636 | B2 * | 6/2008 | Baarman et al. | 363/97 |
| 7,518,267 | B2 * | 4/2009 | Baarman | 307/150 |
| 7,522,878 | B2 * | 4/2009 | Baarman | 455/41.1 |
| 7,554,316 | B2 * | 6/2009 | Stevens et al. | 323/355 |
| 7,639,514 | B2 * | 12/2009 | Baarman | 363/16 |
| 2002/0082059 | A1 | 6/2002 | Nariai et al. | |
| 2002/0154518 | A1 | 10/2002 | Elferich | |
| 2003/0006880 | A1 | 1/2003 | Zimmer | |
| 2003/0015479 | A1 | 1/2003 | Kuennen et al. | |
| 2003/0030342 | A1 | 2/2003 | Chen et al. | 310/102 R |
| 2003/0103039 | A1 | 6/2003 | Burr et al. | 345/163 |
| 2003/0210106 | A1 | 11/2003 | Cheng et al. | |
| 2003/0214821 | A1 | 11/2003 | Giannopoulos | |
| 2004/0130915 | A1 | 7/2004 | Baarman | |
| 2004/0130916 | A1 | 7/2004 | Baarman | |
| 2004/0145342 | A1 | 7/2004 | Lyon | |
| 2005/0007067 | A1 | 1/2005 | Baarman et al. | |
| 2010/0171367 | A1 | 7/2010 | Kitamura et al. | |

FOREIGN PATENT DOCUMENTS

| | | |
|---|---|---|
| EP | 0267009 | 5/1988 |
| EP | 0558316 | 1/1993 |
| EP | 0558316 | 2/1993 |
| EP | 1096641 | 5/2001 |
| GB | 2124042 | 2/1984 |
| GB | 2388715 | 11/2003 |
| GB | 2388716 | 11/2003 |
| JP | 5978496 | 5/1984 |
| JP | 6196699 | 5/1986 |
| JP | 04183274 | 6/1992 |
| JP | 07153577 | 6/1995 |
| JP | 7507917 | 8/1995 |
| JP | 8506927 | 7/1996 |
| JP | H8-214473 | 8/1996 |
| JP | 8298778 | 11/1996 |
| JP | 09-103037 | 4/1997 |
| JP | 09266081 | 10/1997 |
| JP | 10012197 | 1/1998 |
| JP | 10041089 | 2/1998 |
| JP | 10-225129 | 8/1998 |
| JP | H10-215530 | 8/1998 |
| JP | H10-233235 | 9/1998 |
| JP | 3840765 | 6/1999 |
| JP | 11188113 | 7/1999 |
| JP | H11-188113 | 7/1999 |
| JP | H11155245 | 7/1999 |
| JP | 2000-295796 | 10/2000 |
| JP | 2001-128375 | 5/2001 |
| JP | 2001-238372 | 8/2001 |
| JP | 2001238372 | 8/2001 |
| WO | 9419919 | 9/1994 |
| WO | 9422209 | 9/1994 |
| WO | WO 00/54387 | 9/2000 |
| WO | WO0054387 | 9/2000 |
| WO | 0078678 | 12/2000 |
| WO | WO00/54387 | 2/2001 |
| WO | WO 01/80396 A1 | 10/2001 |
| WO | WO 03/096361 | 11/2003 |

OTHER PUBLICATIONS

PCT International Search Report of PCT/US2004/001627, dated Jan. 22, 2004 and Written Opinion of PCT/US2004/0001627, dated Jan. 22, 2004.

PCT International Search Report of PCT/US2004/001758, dated Jan. 22, 2004 and Written Opinion of PCT/US2004/001758, dated Jan. 22, 2004.

Japanese Office Action, Patent Application 2005-304983, Jun. 2, 2008.

Current Control of Quantum Series Resonant Inverter and Application for a DC Motor Drive, Korea Advanced Institute of Science and Technology since 1971, Advisor: Myung Joong Youn by Gun-Woo Moon, Department of Electrical Engineering Korea Advanced Institute of Science and Technology, Dec. 28, 1991.

Malik E. Elbuluk, Member IEEE, George C. Verghese, member IEEE, and John G. Kassakian, Senior Member, IEEE, Sampled-Data Modeling and Digital Control of Resonant Converters, IEEE Transactions on Power Electronics, vol. 3, No. 3. Jul. 1988.

Gyu B. Joung, Chun T. Rim, and Gyu H. Cho, Integral Cycle Mode Control of the Series Resonant Converter, IEEE Transactions on Power Electronics, vol. 4, No. 1, Jan. 1989.

US 4,658,187, 4/1987, Grubbs (withdrawn).

Japanese Office Action, Patent Application 2005-304983, Apr. 22, 2009.

Korean Office Action, Korean Patent Application No. 10-2009-7015863.

* cited by examiner

| Dev. | ID # | Voltage | Current | Status |
|------|-------|---------|---------|--------|
| -1-  | 12345 | 4.0V    | 100 mA  | ON     |
| -2-  | 12346 | 2.5V    | 1000 mA | OFF    |
| -3-  | 12347 | 1.0V    | 10 mA   | CH     |

SYSTEM AND METHOD FOR INDUCTIVE POWER SUPPLY CONTROL USING REMOTE DEVICE POWER REQUIREMENTS

RELATED APPLICATIONS

This application is a continuation of U.S. application Ser. No. 10/689,148 filed Oct. 20, 2003, which claims priority to and benefit of U.S. Provisional Application No. 60/444,794, entitled Adaptively Inductively Coupled Ballast Circuit, by David W. Baarman, filed Feb. 4, 2003. The full disclosure of the prior application is incorporated herein by reference. U.S. application Ser. No. 10/689,148 is a continuation-in-part of U.S. patent application Ser. No. 10/175,095 entitled Fluid Treatment System, which was filed on Jun. 18, 2002, which is a continuation-in-part of U.S. patent application Ser. No. 09/592,194, entitled Fluid Treatment System, which was filed on Jun. 12, 2000. U.S. patent application Ser. No. 09/592,194 claims the benefit under 35 U.S.C. §119(e) of U.S. provisional patent application Ser. No. 60/140,159 entitled Water Treatment System with an Inductively Coupled Ballast, which was filed on Jun. 21, 1999, and U.S. provisional patent application Ser. No. 60/140,090, entitled Point-of-Use Water Treatment System, which was filed on Jun. 21, 1999.

This application incorporates by reference the following applications, which were all filed on Oct. 20, 2003: Adaptive Inductive Power Supply, Ser. No. 10/689,49; Inductive Coil Assembly, Ser. No. 10/689,224; and Adapter, Ser. No. 10/689,375.

BACKGROUND OF THE INVENTION

This invention relates generally to contactless power supplies, and more specifically to contactless power supplies capable of communicating with any devices receiving power from the contactless power supplies.

Contactless energy transmission systems (CEETS) transfers electrical energy from one device to another without any mechanical connection. Because there is no mechanical connection, CEETS have many advantages over conventional energy systems. They are generally safer because there is little danger of sparks or electric shocks due to the isolation of the power supply. They also tend to have a longer life since there are no contacts to become worn. Due to these advantages, CEETS have been used in everything from toothbrushes to portable telephones to trains.

CEETS are composed of power supplies and remote devices. The remote device could be chargeable devices such as batteries, micro-capacitors, or any other chargeable energy source. Alternatively, CEETS could directly power the remote devices.

One kind of CEETS uses magnetic induction to transfer energy. Energy from a primary winding in the power supply is transferred inductively to a secondary winding in the chargeable device. Because the secondary winding is physically spaced from the primary winding, the inductive coupling occurs through the air.

Without a physical connection between the primary winding and the secondary winding, conventional feedback control is not present. Thus, control of the energy transfer in a CEETS from the primary to the secondary is difficult.

One common solution is to design a CEETS dedicated to one type of device. For example, a CEETS for a rechargeable toothbrush is designed only for recharging a toothbrush, while a CEETS for a rechargeable telephone works only with a specific type of telephone. While this solution allows the CEET to operate effectively with one particular device, it fails to be sufficiently flexible to allow the power supply to operate with different remote devices.

Further, since the remote device could be an electronic device capable of performing various tasks, communication with the remote device is desirable. One such system is described in U.S. Pat. No. 6,597,076, in which an actuator powered by a CEET communicates with a process computer in order to provide information relating to up-to-date actuator information. The remote device communicates with a transceiver located at a central processor. Direct communication between the CEET and the actuator is not, however, provided.

In a system shown in U.S. Pat. No. 5,455,466, a portable electronic device receives power from a CEET. Communication between a computer and the portable electronic device is provided by way of the CEET. The CEET acts as a pipeline between the portable electronic device and the computer. The CEET does not obtain information related to the operation of the CEET from the remote device.

While these prior art systems do provide communication, they fail to provide a method or means for the remote device to supply information which could be helpful to the operation of the CEET. For example, a CEET with an adjustable power output could use power requirements from the remote device to operate more efficiently by adjusting its power output. Thus, enabling a CEET to communicate with a remote device in order to obtain power requirements from that remote device is highly desirable.

SUMMARY OF THE INVENTION

A contactless power supply has a resonant circuit having a variable resonant frequency and a primary winding for transferring power to a remote device. The contactless power supply also may have a receiver for communicating with the remote device. The remote device sends power information to the controller. The controller then modifies the operation of the resonant circuit in response to the power information. Thus, the controller can precisely calibrate the power supply for operation with the remote device, providing high efficiency power transfer from the contactless power supply to the remote device.

The contactless power supply could have an inverter and a power source in addition to the resonant circuit coupled to the inverter. In order to achieve high efficiency power transfer, the controller can modify the rail voltage of the power supply, the frequency of operation of the inverter, the duty cycle of the inverter as well as the resonant frequency of the resonant circuit.

The contactless power supply can also be provided with a memory for storing the power information received from the remote device.

The contactless power supply could also operate with a number of remote devices. The contactless power supply would then receiver power information from each of the remote devices. A list of the power information for each of the remote devices is maintained. Based upon the list, the controller determines an optimal settings for the rail voltage, resonant frequency or the duty cycle based upon the list.

The contactless power supply may also have a communication interface for communicating with a workstation. The controller would create a communication link between the workstation and the remote device by way of a transceiver.

The remote device has a remote device controller and a secondary winding having a secondary winding variable impedance. The remote device controller is capable of varying the secondary winding variable impedance. The remote device has a remote device transceiver for communicating with the contactless power supply. The remote device controller varies the secondary winding variable impedance based upon information from the contactless power supply. The remote device's controller could also disable the operation of the remote device based upon information from the contactless power supply. Thus, the remote device could also be operated at a high efficiency.

Thus, the system allows the optimization of both the power supply as well as the device attached to the power supply.

The contactless power and remote devices operate by each remote device sending power usage information to the controller and then adapting the contactless power supply in response to the power usage information. The adaptation of the contactless power supply includes changing the duty cycle, the inverter frequency, the resonant frequency, or the rail voltage.

The power supply could also determine whether the contactless power supply is capable of supplying power to the plurality of remote devices. If not, some of the remote devices could be turned off.

The contactless power supply, the remote device, and the method of operating the power supply and the remote device result in an extremely efficient and very adaptable method of energizing a variety of devices from the power supply. By continually adapting to the addition or removal of loads to the contactless power supply, the contactless power supply remains highly efficient.

These and other objects, advantages and features of the invention will be more readily understood and appreciated by reference to the detailed description of the drawings.

DETAILED DESCRIPTION OF THE DRAWINGS

For purposes of disclosure, the present invention is described in connection with a resonance-seeking ballast circuit, and more particularly in connection with the inductive ballast described in U.S. patent application Ser. No. 10/246, 155 entitled "Inductively Coupled Ballast Circuit," which is incorporated in its entirety by reference into this application. The present invention is, however, well suited for use with other inductive ballast circuits.

Figure 1:
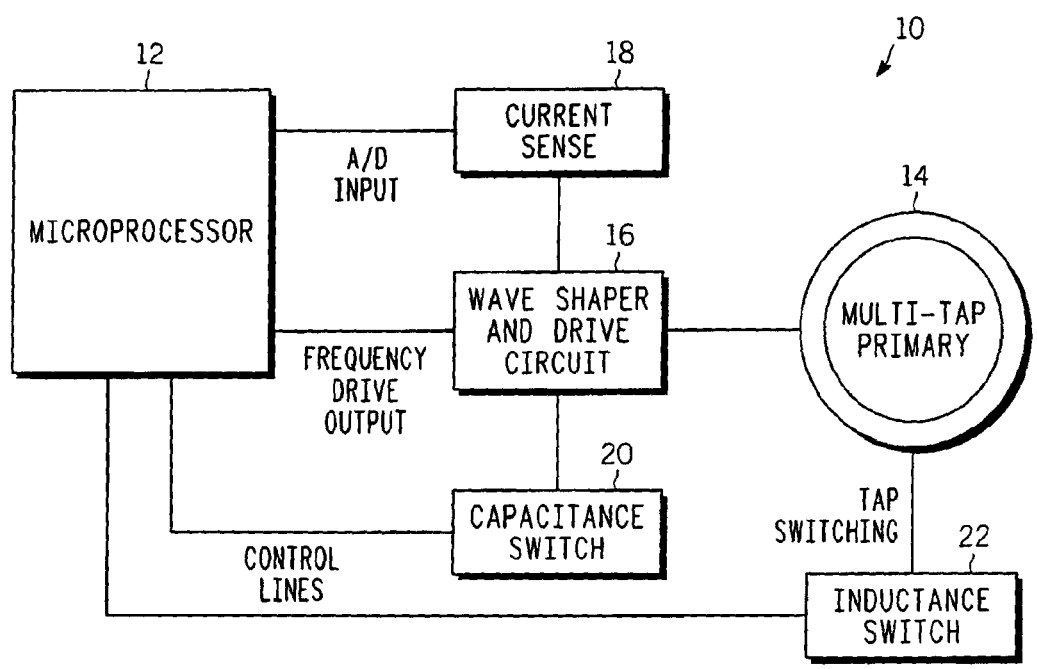
FIG. 1 is a block diagram of an adaptive inductive ballast in accordance with one embodiment of the present invention.

A block diagram showing the general construction of an adaptive inductive ballast 10 in accordance with one embodiment of the present invention is shown in FIG. 1. As illustrated, the adaptive inductive ballast 10 generally includes a microprocessor 12 that controls operation of the circuit, a multi-tap primary 14 for generating a magnetic field, a wave shaper and drive subcircuit 16 that generates the signal applied to the primary 14, a current sense subcircuit 18 that monitors the signal applied to the primary 14 and provides corresponding feedback to the microprocessor 12, a capacitance switch 20 for adjusting the capacitance values in the wave shaper and drive subcircuit 16, and an inductance switch 22 for adjusting the inductance of the multi-tap primary 14. The microprocessor is a conventional microprocessor widely available from a variety of suppliers.

The capacitance switch 20 generally includes two banks of capacitors and a plurality of switches, such as transistors, that are selectively actuatable by the microprocessor 12 to control the values of the two capacitor banks. The capacitors in each bank can be arranged in series or parallel depending on the desired range and distribution of possible capacitance values. The first bank of capacitors replace capacitor 271. Similarly, the second back of capacitors replace capacitor 272 of the pre-existing resonance-seeking ballast shown in the attached patent application. In effect, the capacitance switch 20 makes capacitors 271 and 272 from the pre-existing resonance-seeking ballast into variable capacitors, the values of which are controlled by the microprocessor 12. Alternatively, the described capacitance switch 20 can be replaced by other circuitry capable of providing variable capacitance.

The inductance switch 22 generally includes a multi-tap primary 14 and a plurality of switches, such as transistors, that are selectively actual by the microprocessor 12 to control the values of the inductance of the primary 14. The multi-tap primary 14 replaces primary 270 of the pre-existing resonance-seeking ballast. In effect, the inductance switch 22 makes primary 270 from the pre-existing resonance-seeking ballast into a variable inductance coil by varying the number of turns in the primary 14, the value of which is controlled by the microprocessor 12. Alternatively, the described inductance switch 22 can be replaced by other circuitry capable of providing variable inductance.

In general operation, the microprocessor 12 is programmed to receive input from the current sense subcircuit 18, which is indicative of the current applied to the primary 14. The microprocessor 12 is programmed to separately adjust the capacitance switch 20 and the inductance switch 22 to cycle through the range of capacitance values and inductance values available to the circuit. The microprocessor 12 continues to monitor the input from the current sense circuit 18 while adjusting the capacitance and inductance values to determine which values provide optimum current to the primary 14. The microprocessor 12 then locks the adaptive ballast into the optimum settings.

Figure 2:
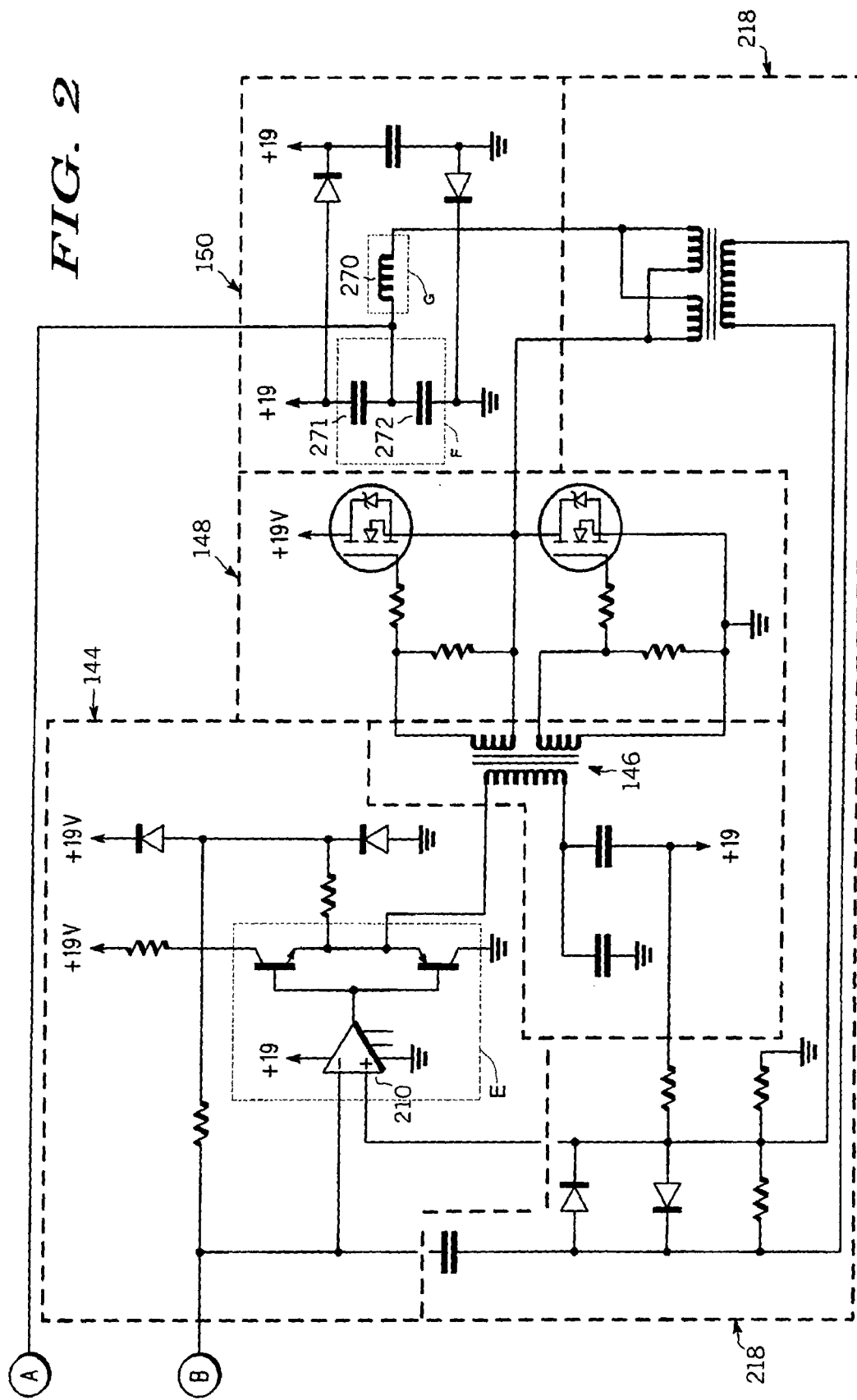
FIG. 2 is a schematic diagram of the resonance-seeking ballast of the attached patent application marked to show changes to incorporate the adaptive inductive ballast of the present invention.

Some of the changes required to adapt the resonance-seeking inductive ballast of the prior patent application into an embodiment of the adaptive inductive ballast circuit 10 are noted in the schematic diagram of FIG. 2.

While the pre-existing resonance-seeking ballast is described in greater detail in U.S. patent application Ser. No. 10/246,155, an overview of the circuit may be helpful to a fuller understanding of this invention. A ballast feedback circuit is connected at point A and a control circuit is connected at point B. Oscillator 144 provides half bridge inverter 148 with an alternating signal by way of drive 146. Half bridge inverter powers tank circuit 150. Current sensing circuit 218 provides feedback to oscillator 144. The feedback circuit, control circuit, oscillator, half bridge inverter, drive and current sensing circuit 218 as well as other supporting circuitry is more fully described in the above referenced patent application.

In FIG. 2, a phase delay could be inserted at E and can be controlled as a delay line. This delay can be used to throttle the phase and control secondary amplitude. At F, switched capacitance can adjust the resonant frequency based on the adjustable primary inductance. Simple transistors can be used to switch in and out capacitance. The capacitance is changed when the primary inductor changes as to match load. At G, primary inductance can be switched to adjust the power required by the secondary circuit. RFID or direct communications can indicate the needed load. With that load information, the control processor can adjust the inductance as needed to provide the power required. The inductance can be switched using transistors and multiple taps from the primary inductor controlled by the microprocessor.

Figure 3:
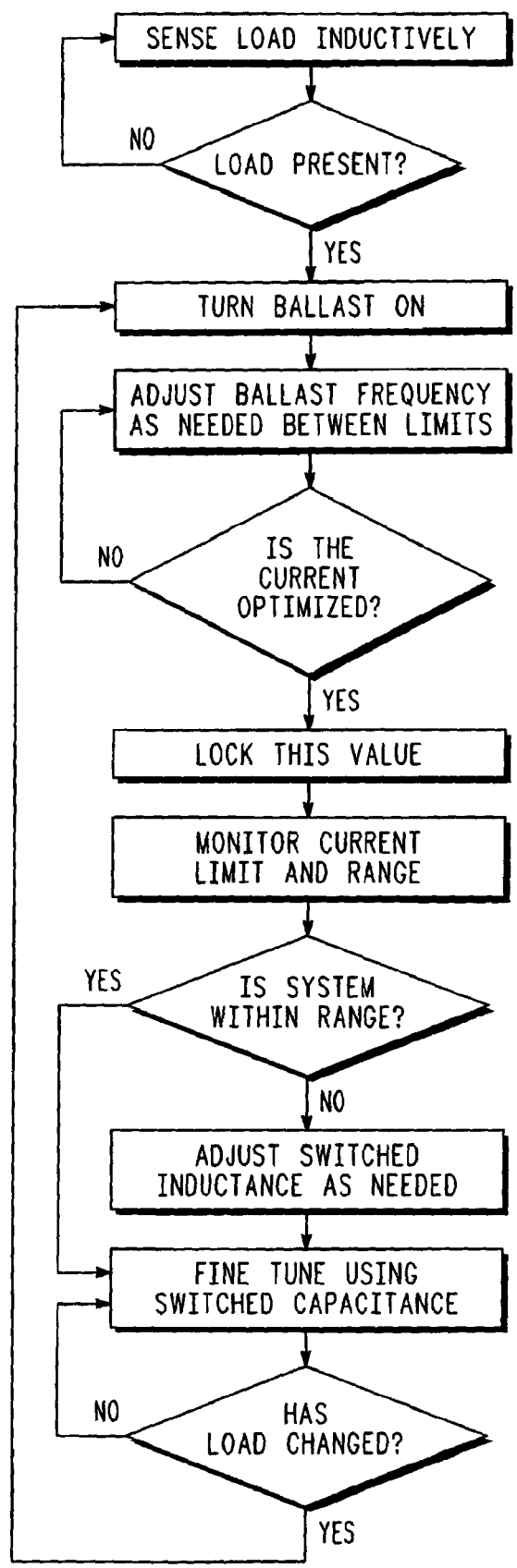
FIG. 3 is a flow chart illustrating operation of the adaptive inductive ballast.

The operating sequence of the adaptive inductive ballast circuit is described in more detail in connection with FIG. 3. In operation, the illustrated system waits until it determines that a load is present before applying power to the primary 14. This will save power and may be done by providing each inductively powered device with a magnet that actuates a reed switch adjacent to the primary. Alternatively, a user-actuated switch (not shown) may be provided so that the user can engage the power supply when an inductively powered device is present. As another alternative, the inductively powered device may be configured to mechanically actuate a switch when it is placed into proximity with the primary to signal its presence. As a further alternative, the switching mechanism can be eliminated and the ballast circuit can provide power to the primary 14 regardless of the presence of a load.

Once the power supply circuit is activated, the circuit adjusts its frequency to optimize the current applied to the primary. After the appropriate operating frequency has been determined at initial capacitance and inductance values, the microprocessor locks the ballast circuit into the operating frequency and then begins to cycle through the range of inductance values available through the multi-tap primary. After each change in inductance value, the microprocessor unlocks the operating frequency and permits the ballast circuit to seek resonance, settling at a frequency that provides optimal current to the primary. The microprocessor continues cycling through the available inductance values until it has determined which value provides optimal current to the primary. In one embodiment, a progressive scanning process is used to determine the appropriate inductance value. This is achieved by starting the scanning process with the lowest inductance value, and sequentially stepping up the inductance value until the change in inductance value results in a reduction in the current applied to the primary. The microprocessor will then step back down one inductance value, where the greatest current was achieved. Alternatively, the scanning process may begin with the highest inductance value, and sequentially step down the inductance value until the change in inductance value results in a reduction in the current applied to the primary. The microprocessor will then step back up one inductance value, where the greatest current was achieved. As another alternative, the microprocessor can step through each inductance value to determine the corresponding current, and after stepping through each value, return to the inductance value that provided the greatest current to the primary.

After the appropriate inductance value is determined, the microprocessor locks the circuit at the determined inductance value and begins to cycle through the capacitance values. In one embodiment, the microprocessor uses a progressive scanning technique to determine the capacitance that provides the primary with the greatest current. The scanning process may progress upwardly from the lowest capacitance value or downwardly from the highest capacitance value, as described above in connection with the scanning process for the inductance value. As an alternative to a progressive scanning process, the microprocessor can step through each capacitance value to determine the corresponding current, and after stepping through each value, return to the capacitance value that provided the greatest current to the primary.

In this embodiment, the frequency of the ballast circuit is not permitted to vary once the appropriate inductance value has been determined. The microprocessor can, alternatively, be programmed to permit the ballast circuit to seek resonance after each change in capacitance value.

In an alternative embodiment, the microprocessor may be programmed to provide adjustment of only the capacitance value or only the inductance value of the power supply circuit. In the former alternative, the multi-tap primary can be replaced by a conventional single-tap primary and the inductance switch can be eliminated. In the latter alternative, the capacitor bank can be replaced by a single set of capacitors and the capacitance switch can be eliminated. In another alternative embodiment, the microprocessor can be programmed to adjust the capacitance before adjusting the inductance.

As noted above, the present invention is not limited to use in connection with a resonance-seeking ballast. In other applications, a current sensor may be incorporated into the ballast to provide input to the microprocessor that is representative of the current being applied to the primary. In operation without a resonance-seeking ballast, the microprocessor will separately cycle through the various capacitance and inductance values to determine the values that provide optimum power to the primary.

In a further alternative embodiment, the adaptive inductive ballast 10 may include phase delay circuitry (not shown) that permits the ballast 10 to throttle the phase and control secondary amplitude. The phase delay circuitry may include a delay line or a Digital Signal Processor (DSP) that is connected to the wave shaper and drive circuit 16 following the operational amplifier 210.

A further alternative embodiment of the present invention is described in connection with FIGS. 4-5. In this embodiment, the adaptive inductive ballast 10' and the inductively powered device have the ability to communicate, for example, using conventional RF communications or direct communications.

Figure 4:
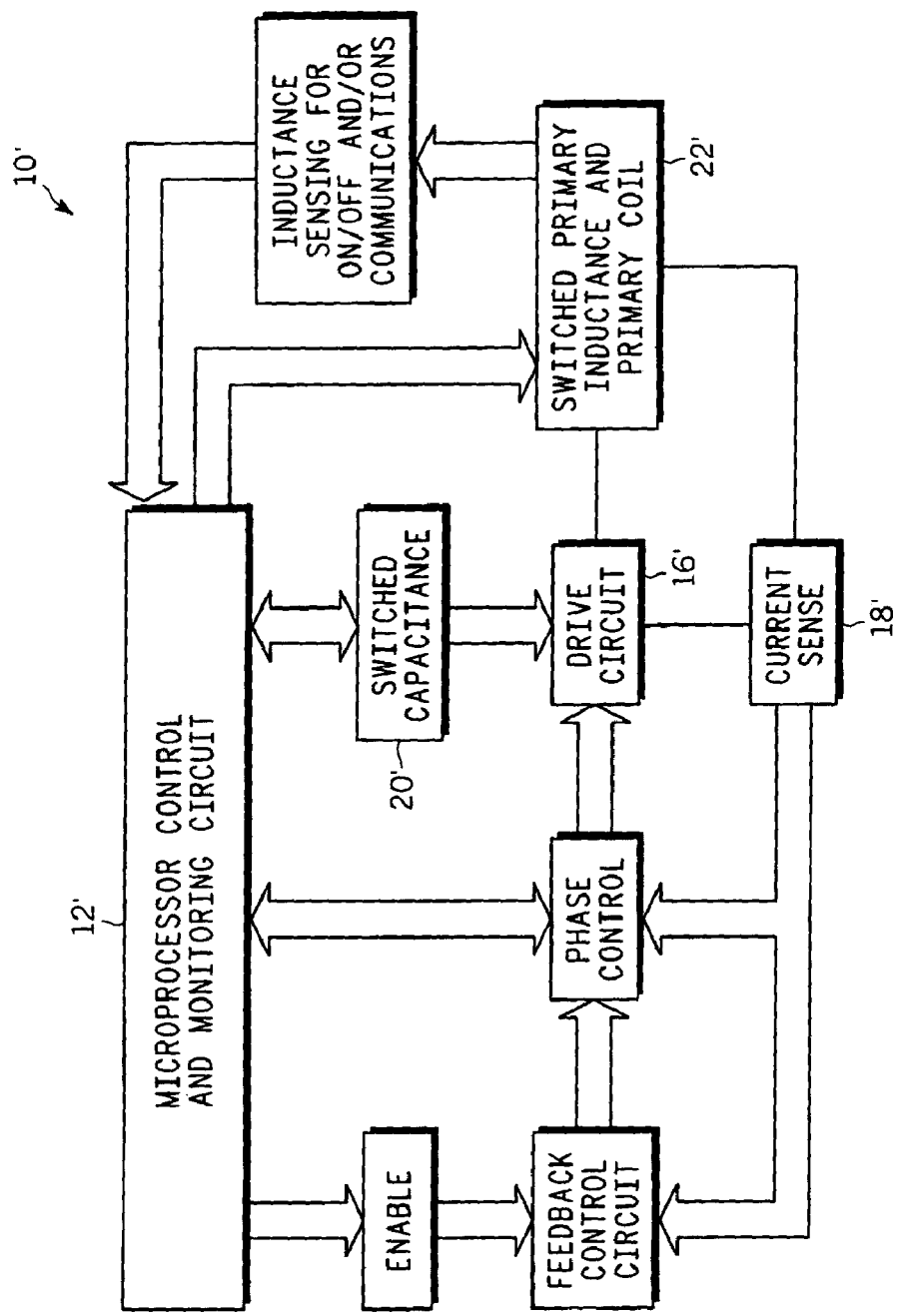
FIG. 4 is a block diagram of an alternative embodiment incorporating RF communications and phase control.
Figure 5:
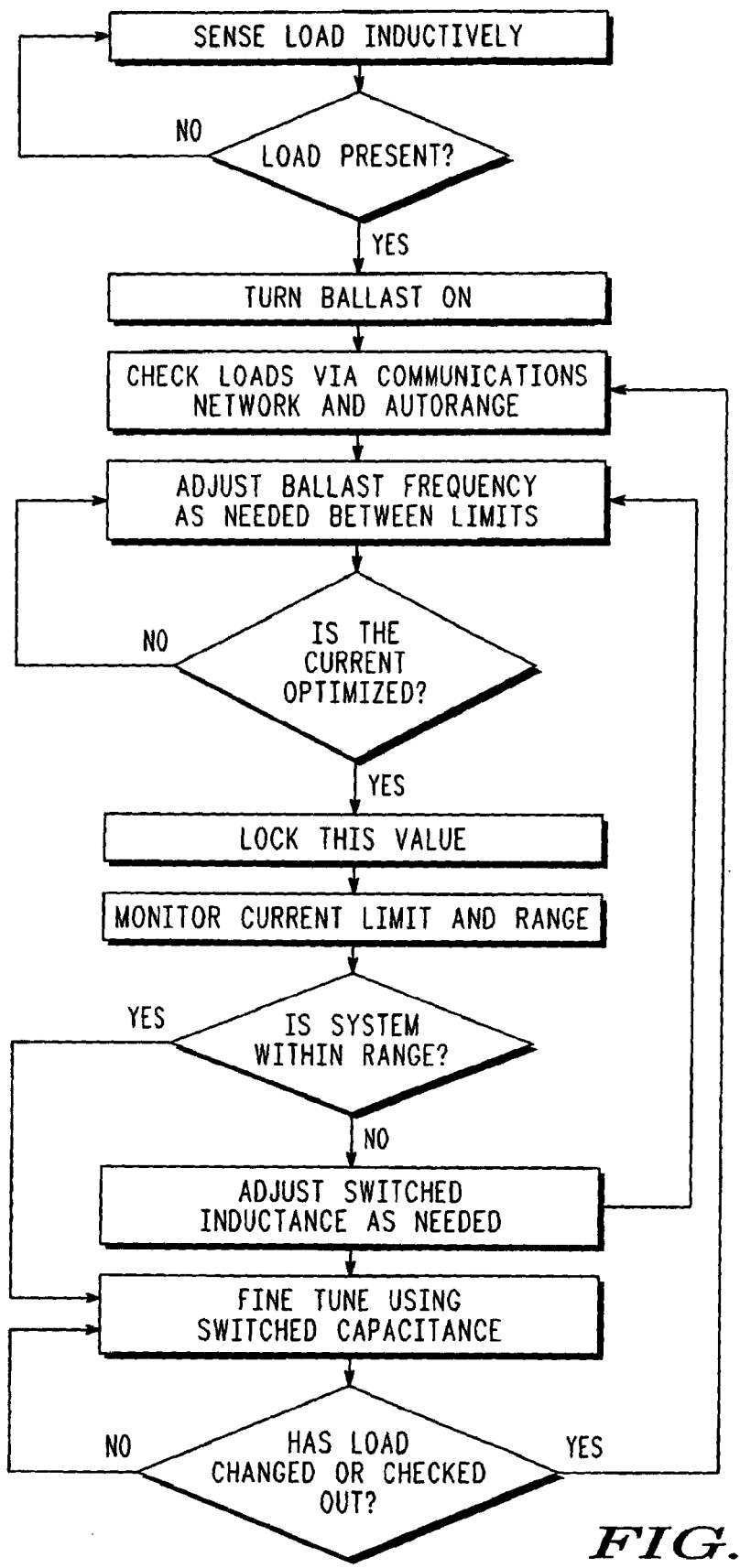
FIG. 5 is a flow chart illustrating operation of the adaptive inductive ballast incorporating communications capability

FIG. 4 is a block diagram showing the general components of the adaptive inductive ballast 10'. The adaptive inductive ballast 10' includes a communication coil (not shown) that is separate from the switched primary inductance and primary coil 22'. The communication coil could be part of the primary. The communication coil is connected to the microprocessor 12', which is programmed to receive the information from the inductively powered device and to effect operation of the adaptive inductive ballast 10' based on that information. The inductively powered device also includes a communication coil that could be separate from or integral with the secondary that receives power from the primary. The inductively powered load and the adaptive inductive power supply 10' communicate using conventional communications techniques and apparatus, for example, using standard communications circuitry and standard communications protocol.

Operation of the adaptive ballast 10' is generally identical to that of ballast 10 described above, except as noted below. A flow chart showing the general steps of operation of the ballast 10' is show in FIG. 5. Through the use of its communications capability, the inductively powered device can relay load information to the adaptive inductive ballast 10', such as the wattage of the load. The adaptive inductive ballast 10' can use this information in determining the appropriate capacitance and inductance values. More specifically, this information can be used to ensure that the primary of switched primary inductance and primary coil 22' is operating at the correct wattage. If not, the switched primary inductance of switched primary inductance and primary coil 22' and capacitance switch 20' can be used to adjust the wattage of the primary. This embodiment may, in some applications, provide improved operation over adaptive inductive ballast 10 described above because it does not necessarily drive the primary at its highest possible current value. Instead, this embodiment matches the power output of the primary to the power requirements of the inductively powered device, meaning that it may reduce power and save energy when full power is not required.

The aforementioned system of FIGS. 1-5 is further enhanced and explained with reference to FIGS. 6-9.

Figure 6:
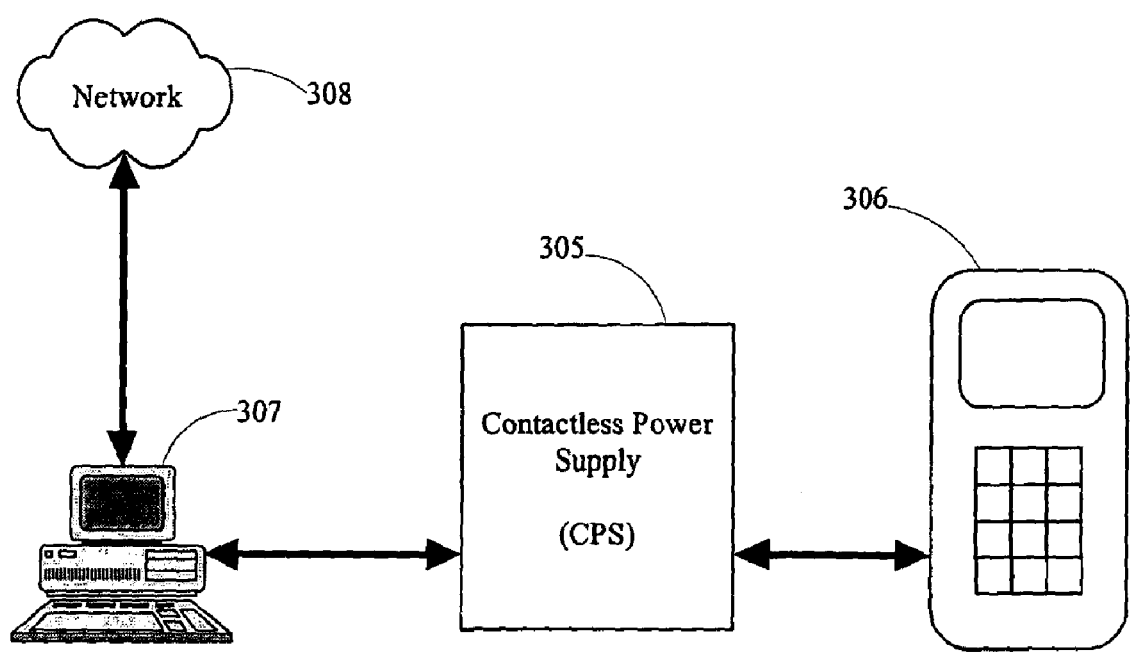
FIG. 6 shows a contactless energy transmission system connected to a remote device and a workstation.

FIG. 6 shows an adaptive contactless energy transmission system incorporating one embodiment of the present invention. Contactless power supply 305 is inductively coupled to remote device 306. Contactless power supply 305 is also connected to workstation 307. Network 308 is, in turn, connected to workstation 307.

In one embodiment, contactless power supply 305 establishes a communication link between workstation 307 and remote device 306, allowing information to be transmitted to and from remote device 306. If remote device 306 were a PDA (personal digital assistant), information from the PDA could be exchanged with workstation 307. For example, a PDA could automatically synchronize a calendar and an address list while the PDA was charging. As another example, if remote device 306 were an MP3 player, then songs could be downloaded to and from the MP3 player while the MP3 player was charging.

Figure 7:
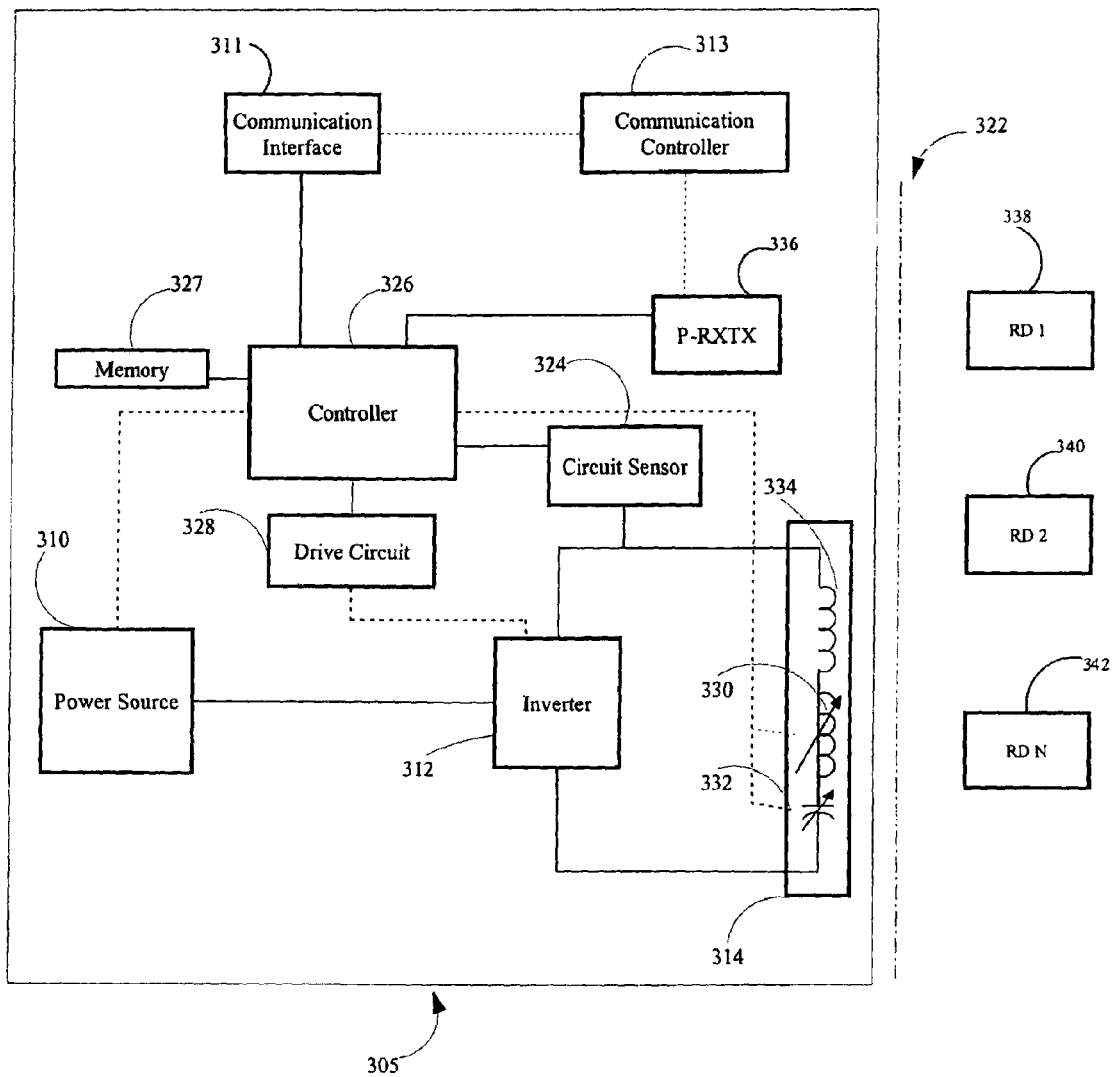
FIG. 7 is a block diagram for an adaptive contactless energy transmission system with communications capability.

FIG. 7 shows a block diagram for an embodiment of an adaptive contactless energy transmission system with communication for communicating with a plurality of remote devices.

The adaptive contactless energy transmission system has contactless power supply 305 and remote device 338, 340, 342.

As is well know, power source 310 is a DC power source providing DC (direct current) power to inverter 312. Inverter 312 converts the DC power to AC (alternating current) power. Inverter 312 acts as an AC power source supplying the AC power to tank circuit 314. Tank circuit 314 is a resonant circuit. Tank circuit 314 is inductively coupled to secondary winding 316 of remote device 338.

The secondary windings of remote devices 338, 340, 342 have no core. Dashed line 320 indicates an air gap between remote devices 338, 340, 342 and power supply 305.

Circuit sensor 324 is coupled to the output of tank circuit 314. Circuit sensor 324 is also coupled to controller 326. Circuit sensor 324 provides information regarding the operational parameters of the power supply. For example, circuit sensor could be a current sensor and provide information regarding the phase, frequency and amplitude of the current in tank circuit 314.

Controller 326 could be any one of a multitude of commonly available microcontrollers programmed to perform the functions hereinafter described, such as the Intel 8051 or the Motorola 6811, or any of the many variants of those microcontrollers. Controller 326 could have a ROM (read only memory) and RAM (random access memory) on the chip. Controller 326 could have a series of analog and digital outputs for controlling the various functions within the adaptive inductive power supply.

Controller 326 is connected to memory 327. Controller 326 is also coupled to drive circuit 328. Drive circuit 328 regulates the operation of inverter 312. Drive circuit 328 regulates the frequency and timing of inverter 312. Controller 326 is also coupled to power source 310. Controller 326 can manipulate the rail voltage of power source 310. As is well known, by altering the rail voltage of power source 310, the amplitude of the output of inverter 312 is also altered.

Finally, controller 326 is coupled to variable inductor 330 and variable capacitor 332 of tank circuit 314. Controller 326 can modify the inductance of variable inductor 330 or the capacitance of variable capacitor 332. By modifying the inductance of variable inductor 330 and the capacitance of variable capacitor 332, the resonant frequency of tank circuit 314 can be changed.

Tank circuit 314 could have a first resonant frequency and a second resonant frequency. Tank circuit 314 could also have several resonant frequencies. As used herein, the term "resonant frequency" refers to a band of frequencies within which tank circuit 314 will resonate. As is well known, a tank circuit will have a resonant frequency, but will continue to resonate within a range of frequencies. Tank circuit 314 has at least one variable impedance element having a variable impedance. By varying the variable impedance, the resonant frequency of the tank circuit will be varied. The variable impedance element could be variable inductor 330 or variable capacitor 332, or both.

Variable inductor 330 could be a thyristor controlled variable inductor, a compressible variable inductor, parallel laminated core variable inductor, a series of inductors and switches capable of placing select fixed inductors into tank circuit 314, or any other controllable variable inductor. Variable capacitor could be a switched capacitor array, a series of fixed capacitors and switches capable of placing select fixed capacitors into tank circuit 314, or any other controllable variable capacitor.

Tank circuit 314 also includes primary winding 334. Primary winding 334 and variable inductor 330 are shown separate. Alternatively, primary winding 334 and variable inductor 330 could be combined into a single element. Tank circuit 314 is shown as a series resonant tank circuit. A parallel resonant tank circuit could also be used.

Power supply transceiver 336 is also coupled to controller. Power supply transceiver 336 could be simply a receiver for receiving information rather than a device enabling two-way communication. Power supply transceiver 336 communicates with various remote device 338, 340, 342. Obviously, more or less devices than three could be used with the system.

In this embodiment, contactless power supply 305 also has communication interface 311 for connection to workstation 307. Communication interface 311 could be any of a number of well known or proprietary interfaces such as USB, firewire, or RS-232. Workstation 307 is connected to network 308. Network 308 could be a LAN (local area network) or the Internet.

Contactless power supply 305 could also have communication controller 313. Communication controller 313 manages data input and output through communication interface 311 and power supply transceiver 336. Communication controller 313 performs necessary control functions such as code conversion, protocol conversion, buffering, data compression, error checking, synchronization and route selection as well as collects management information. Communication controller 313 establishes communication sessions between remote devices 338, 340, 342 and workstation 307 or any other devices within network 308. Communication controller 313 could be a front end processor. Depending upon the capabilities of controller 326, communication controller 313 could be a software module running within controller 326.

Figures 8, 10:
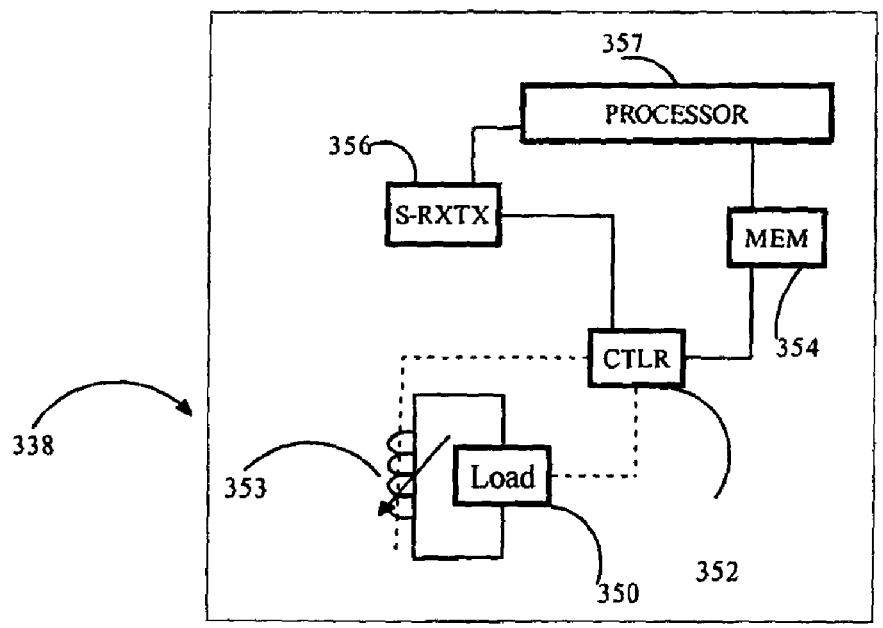
FIG. 8 is a block diagram of a remote device with communications capability.
FIG. 10 is an exemplary list of remote devices powered by a contactless power supply with communications capability.

FIG. 8 shows a block diagram of remote device 338. Remote device 338 is exemplary of remote devices 340, 342 as well. Remote device 338 includes load 350. Load 350 receives power from variable secondary 353. Load 350 could be a rechargeable battery or any other kind of load.

Variable secondary 353 is preferably coreless, allowing variable secondary 353 to operate over a wider range of frequencies. Variable secondary 353 is shown as a variable inductor, although other types of devices could be used in place of the variable inductor.

Remote device controller 352 controls the inductance of variable secondary 353 and the operation of load 350. For example, remote device controller 352 can alter the inductance of variable secondary 353 or turn on or off load 350. Similar to controller 326, remote device controller 352 could be any one of a multitude of commonly available microcontrollers programmed to perform the functions hereinafter described, such as the Intel 8051 or the Motorola 6811, or any of the many variants of those microcontrollers. Controller 352 could have a ROM (read only memory) and RAM (random access memory) on the chip. Controller 352 could also have a series of analog and digital outputs for controlling the various functions within the adaptive inductive power supply.

Memory 354 contains, among other things, a device ID (identification) number and power information about remote device 338. Power information would include the voltage, current and power consumption information for remote device 338. If load 350 were a rechargeable battery, memory 354 might include discharge rates and charging rates.

Remote device 338 also includes remote transceiver 356. Remote transceiver 356 receives and transmits information to and from power supply transceiver 336. Remote transceiver 356 and power supply transceiver 336 could be linked in a myriad of different ways, such as WIFI, infrared, blue tooth, or cellular. Additionally, the transceivers could communicate by way of additional coils on the primary or secondary. Or, since power in being delivered by power supply 305 to remote devices 338, 340, 342, by any one of many different power line communication systems.

Alternatively, remote transceiver 356 could be simply a wireless transmitter for sending information to transceiver 336. For example, remote transceiver 356 could be an RFID (Radio Frequency Identification) tag.

Processor 357 represents the functional component of remote device 338. For example, if remote device 338 were a digital camera, processor 357 could be a microprocessor within the digital camera. If remote device 338 were an MP3 player, processor 357 could be a digital signal processor or a microprocessor and related circuitry for converting MP3 files into sounds. If remote device 338 were a PDA, then processor 357 would be a microprocessor and related circuitry providing the functionality of a PDA. Processor 357 could access memory 354.

Processor 357 is also coupled to secondary device transceiver 356. Thus, processor 357 could communicate through secondary device transceiver 356 with contactless power supply 305, and thereby could communicate with any other devices connected to power supply 305, such as a workstation.

Due to the presence of communication interface 311, remote device 338 could communicate to workstation 307 or the network 308. In order to enable communication between remote device 338 and workstation 307, controller 326 would establish a communication link to remote device 338 by way of transceiver 336.

Figure 9:
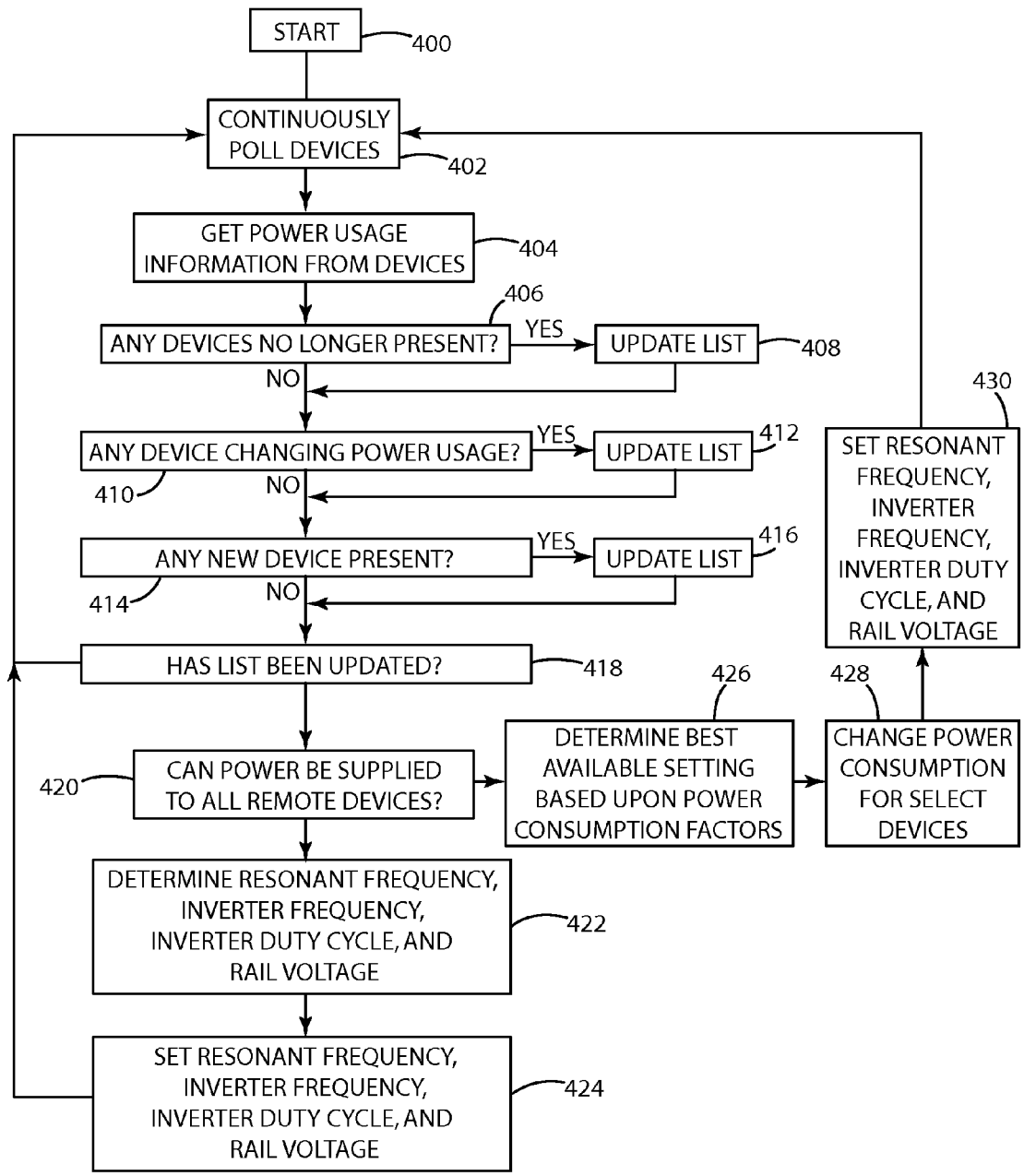
FIG. 9 is a flow chart showing the operating of an adaptive contactless energy transmission system.

FIG. 9 shows the operation of the adaptive contactless energy transmission system with communications capability.

After contactless power supply 305 starts (Step 400), it polls all remote devices by way of transceiver 336. Step 402. Step 402 could be continuous, where advancement to Step 404 occurs only if a remote device is present. Alternatively, the following steps could be performed before polling is repeated, although the operations would be performed with reference to a null set. If any remote device is present, it receives power usage information from the remote device. Step 404.

The power usage information could include actual information regarding voltage, current, and power requirements for remote device 338. Alternatively, power usage information could be simply an ID number for remote device 338. If so, controller 326 would receive the ID number and look up the power requirement for remote device 338 from a table contained in memory 327.

After all devices have been polled and the power information for each device has been received, contactless power supply 305 then determines whether any device is no longer present. If so, then a remote device list is updated. Step 408.

The remote device list maintained by controller 326 is shown in FIG. 10. The remote device list could contain for a device ID, a voltage, a current, and a status for each remote device 338, 340, 342. The device number is assigned by controller 326. The device ID is received from remote devices 338, 340, 342. If two remote devices are the same type, then the device ID could be the same. The voltage and current are the amount of voltage or current required to power the device. The voltage and current could be transmitted discretely by remote devices 338, 340, 342, or they could be obtained by using the device ID as a key to a database of remote devices maintained in memory 327. The status is the current status of the device. For example, the device status could be 'on', 'off', 'charging', etc.

Next, contactless power supply 305 determines whether the status of any device has changed. Step 410. For example, remote device 338 could have a rechargeable battery. When the rechargeable battery is fully charged, remote device 338 would no longer need power. Thus, its status would change from "Charging" to "Off." If the status of the device changes, then the remote device list is updated. Step 412.

Contactless power supply 305 then determines if any devices are present. Step 414. If so, then the remote device list is updated. Step 416. The remote device list is then checked. Step 418. If the list was not updated, the system then polls the devices again, and the process restarts. Step 402.

If the list was updated, then the power usage by the remote devices has changed, and thus the power supplied by contactless power supply 305 must also change. Controller 326 uses the remote device list to determine the power requirements of all the remote devices. It then determines if the system can be reconfigured to adequately power all the devices. Step 420.

If contactless power supply 305 can supply power to all of the remote devices, then controller 326 calculates the settings for inverter frequency, duty cycle, resonant frequency, and rail voltage. Further, controller determines the best setting for the variable impedance of secondary winding 353 of remote devices 338, 340, 342. Step 422. It then sets the inverter frequency, duty cycle, resonant frequency, and rail voltage.

Step 424. It also instructs remote devices 338, 340, 342 to set the variable impedance of secondary winding 353 to the desired level. Step 424.

On the other hand, if contactless power supply 305 cannot supply power to all of the remote devices, controller 326 determines the best possible power settings for the entire system. Step 426. It may then instruct one or more of remote devices 338, 340, 342 to turn off or change its power consumption. Controller determines the best setting for the variable impedance of secondary winding 353 of remote devices 338, 340, 342. Step 428. It then sets the inverter frequency, duty cycle, resonant frequency, and rail voltage for the system. Step 430. Controller instructs remote devices 338, 340, 342 to set the variable impedance of secondary winding 353 at the desired level. The system then returns to polling the devices, and the process repeats. Step 402.

The above description is of the preferred embodiment. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a", "an," "the," or "said," is not to be construed as limiting the element to the singular.

The embodiments of the invention in which an exclusive property or privilege is claimed are defined as follows:

1. A method for supplying power from an inductive power supply to a remote device, said method comprising:
   receiving, in said inductive power supply, a remote device ID from said remote device;
   obtaining remote device power requirement information;
   maintaining an active remote device list in memory, said active remote device list capable of including a plurality of active remote devices;
   configuring said inductive power supply to supply power based on said power requirement information; and
   wherein said obtaining remote device power requirement information includes at least one of (1) obtaining at least one of an amount of voltage and an amount of current required to power said remote device from a database of remote device power requirement information maintained in memory, wherein said remote device ID is a key to said database; and (2) receiving, in said inductive power supply, at least one of an amount of voltage and an amount of current required to power said remote device.

2. The method of claim 1 further comprising receiving a remote device ID from a different remote device.

3. The method of claim 2 wherein both of said remote devices are the same type of device and have the same remote device ID.

4. The method of claim 2 wherein both of said remote devices are the same type of device and have different remote device IDs.

5. The method of claim 2 further comprising assigning a different device number to each remote device.

6. The method of claim 1 wherein maintaining said active remote device list includes updating said active remote device list in response to at least one of a change in status of said remote device and a change in presence of said remote device.

7. A method for supplying power from an inductive power supply to a remote device, said method comprising:
   receiving, in said inductive power supply, a remote device ID from said remote device;
   obtaining remote device power requirement information;
   maintaining an active remote device list in memory, said active remote device list capable of including a plurality of active remote devices;
   configuring said inductive power supply to supply power based on said power requirement information; and
   determining whether said inductive power supply can be configured to adequately power all remote devices on said active remote device list.

8. The method of claim 7 further comprising determining inductive power supply settings in response to determining that said inductive power supply can be configured to adequately power all remote devices on said active remote device list.

9. The method of claim 7 further comprising determining inductive power supply settings and instructing at least one remote devices on said active remote device list to change power consumption, in response to determining that said inductive power supply cannot be configured to adequately power all remote devices on said active remote device list.

10. An inductive power supply for supplying power to a remote device, said inductive power supply comprising:
    a receiver configured to receive a remote device ID from said remote device;
    a primary configured to transfer power to said remote device;
    a memory; and
    a controller in communication with said receiver, said primary, and said memory, said controller programmed to:
      obtain remote device power requirement information;
      maintain an active remote device list in said memory, said active remote device list capable of including a plurality of active remote devices;
      configure said inductive power supply to supply power based on said power requirement information; and
      wherein said controller is programmed to obtain remote device power requirement information by at least one of (1) obtaining at least one of an amount of voltage and an amount of current required to power said remote device from a database of remote device power requirement information maintained in memory, wherein said device ID is a key to said database; and (2) receiving at least one of an amount of voltage and an amount of current required to power said remote device from said remote device via said receiver.

11. The inductive power supply of claim 10 further comprising receiving a remote device ID from a different remote device.

12. The inductive power supply of claim 11 wherein both of said remote devices are the same type of device and have the same remote device ID.

13. The inductive power supply of claim 11 wherein both of said remote devices are the same type of device and have different remote device IDs.

14. The inductive power supply of claim 11 wherein said controller is programmed to assign a different device number to each remote device.

15. The inductive power supply of claim 10 wherein said controller is programmed to maintain said active remote device list in said memory by updating said active remote device list in response to at least one of a change in status of said remote device and a change in presence of said remote device.

16. An inductive power supply for supplying power to a remote device, said inductive power supply comprising:
    a receiver configured to receive a remote device ID from said remote device;

a primary configured to transfer power to said remote device;
a memory; and
a controller in communication with said receiver, said primary, and said memory, said controller programmed to:
obtain remote device power requirement information;
maintain an active remote device list in said memory, said active remote device list capable of including a plurality of active remote devices;
configure said inductive power supply to supply power based on said power requirement information; and
wherein said controller is programmed to determine whether said inductive power supply can be configured to adequately power all remote devices on said active remote device list.

17. The inductive power supply of claim 16 wherein said controller is programmed to determine inductive power supply settings in response to determining that said inductive power supply can be configured to adequately power all devices on said active remote device list.

18. The inductive power supply of claim 16 wherein said controller is programmed to determine inductive power supply settings and instruct at least one device on said active remote device list to change power consumption, in response to determining that said inductive power supply cannot be configured to adequately power all of said plurality of remote devices.

19. The inductive power supply of claim 16 wherein said receiver comprises at least one of a communication coil, an RF communication system, and said primary.

20. A method for supplying power from an inductive power supply to a plurality of remote devices, said method comprising:
polling said plurality of remote devices for power usage information;
receiving, in the inductive power supply, power usage information for each of said plurality of remote devices;
obtaining remote device power requirement information for each of said plurality of remote devices;
maintaining an active remote device list in memory, said active remote device list capable of including a plurality of active remote devices;
determining whether said inductive power supply can be configured to adequately power all devices on said active remote device list;
adjusting power consumption characteristics of at least one of said plurality of remote devices in response to a determination that power cannot be supplied to all devices on said active remote device list; and
configuring said inductive power supply to supply power based on said power requirement information.

21. The method of claim 20 wherein said obtaining remote device power requirement information for each of said plurality of remote devices includes at least one of (1) obtaining at least one of an amount of voltage and an amount of current required from a database of remote device power requirement information maintained in memory, wherein said power usage information for each of said plurality of remote devices includes a device ID that is a key to said database; and (2) said receiving, in said inductive power supply, power usage information for each of said plurality of remote devices, wherein said power usage information includes at least one of an amount of voltage and an amount of current required to power said remote device.

22. The method of claim 20 further comprising updating said active remote device list in response to a change in status of any of said plurality of remote devices and a change in presence of any of said plurality of remote devices.

23. The method of claim 20 further comprising determining inductive power supply settings in response to determining that said inductive power supply can be configured to adequately power all devices on said active remote device list.

24. An inductive power supply for supplying power to a plurality of remote devices, the inductive power supply comprising:
a transceiver configured to communicate with each of said plurality of remote devices;
a primary;
a memory; and
a controller in communication with said receiver, said primary, and said memory, said controller programmed to:
poll said plurality of remote devices for power usage information via said transceiver;
obtain remote device power requirement information for each of said plurality of remote devices;
maintain an active remote device list in said memory, said active remote device list capable of including a plurality of active remote devices;
determine whether said inductive power supply can be configured to adequately power all devices on said active remote device list;
adjust power consumption characteristics of at least one of said plurality of remote devices in response to a determination that power cannot be supplied to all devices on said active remote device list; and
configure said inductive power supply to supply power based on said power requirement information.

25. The inductive power supply of claim 24 wherein said controller is programmed to obtain remote device power requirement information for each remote device by at least one of (1) obtaining at least one of an amount of voltage and an amount of current required from a database of remote device power requirement information maintained in memory, wherein said device ID is a key to said database; and (2) receiving at least one of an amount of voltage and an amount of current required to power said remote device from said remote device via said transceiver.

26. The inductive power supply of claim 25 wherein said controller is programmed to adjust power consumption characteristics of at least one of said plurality of remote devices by instructing at least one remote device on said active remote device list to change power consumption via said transceiver.

27. The inductive power supply of claim 25 wherein said transceiver comprises at least one of a communication coil, an RF communication system, a primary winding.

28. The inductive power supply of claim 24 wherein said controller is programmed to assign a different device number to each remote device.

29. The inductive power supply of claim 24 wherein said controller is programmed to maintain said active remote device list in memory by updating said active remote device list in response to at least one of a change in status of any of said plurality of remote devices and a change in presence of any of said plurality of remote devices.

* * * * *